(12) United States Patent
Idowu et al.

(10) Patent No.: US 10,070,984 B2
(45) Date of Patent: Sep. 11, 2018

(54) VARIABLE PRESSURE UPPER TORSO BRACES AND METHODS RELATED THERETO

(71) Applicant: Children's Hospital & Research Center Oakland, Oakland, CA (US)

(72) Inventors: Olajire Idowu, Lafayette, CA (US); Sunghoon Kim, San Ramon, CA (US)

(73) Assignee: Childrens's Hospital & Research Center at Oakland, Oakland, CA (US)

(*) Notice: Subject to any disclaimer, the term of this patent is extended or adjusted under 35 U.S.C. 154(b) by 0 days.

(21) Appl. No.: 14/649,197

(22) PCT Filed: Nov. 26, 2013

(86) PCT No.: PCT/US2013/072080
§ 371 (c)(1),
(2) Date: Jun. 2, 2015

(87) PCT Pub. No.: WO2014/088894
PCT Pub. Date: Jun. 12, 2014

(65) Prior Publication Data
US 2015/0328035 A1 Nov. 19, 2015

Related U.S. Application Data

(60) Provisional application No. 61/734,310, filed on Dec. 6, 2012.

(51) Int. Cl.
*A61F 5/00* (2006.01)
*A61F 5/02* (2006.01)
(Continued)

(52) U.S. Cl.
CPC .............. *A61F 5/02* (2013.01); *A61F 5/03* (2013.01); *A61F 5/34* (2013.01)

(58) Field of Classification Search
CPC .... A61F 5/01; A61F 5/02; A61F 5/802; A61F 5/022; A61F 5/024; A61F 5/026;
(Continued)

(56) References Cited

U.S. PATENT DOCUMENTS

87,370 A * 3/1869 Schnebly ................. A61F 5/24
128/109.1
197,142 A * 11/1877 Jones ....................... A61F 5/24
128/119.1
(Continued)

*Primary Examiner* — Victoria J Hicks
(74) *Attorney, Agent, or Firm* — Michael B. Rubin; Bozicevic, Field & Francis LLP (57) ABSTRACT

Upper torso braces to correct deformities in the upper torso of a patient are provided. The upper torso braces include a brace structure adapted to be maintained around an upper torso of an individual and to restrict outward expansion, and a variable force applicator coupled to the brace structure and positioned to contact and apply varying pressure to a target location on the upper torso. The brace structure is configured to restrict outward expansion and to provide a counteracting force for the variable force applicator during application of the variable pressure to the target location. In some instances, the upper torso braces may include a control element to adjust an amount of pressure provided by the variable force applicator to the target location. Methods of correcting a deformity on an upper torso with the upper torso braces are also provided.

6 Claims, 7 Drawing Sheets

(51) Int. Cl.
*A61F 5/03* (2006.01)
*A61F 5/34* (2006.01)

(58) Field of Classification Search
CPC .. A61F 5/0258; A61F 5/24; A61F 5/26; A61F
5/30; A61F 5/32; A61F 5/05808; A63B
23/0211; A63B 23/02; A63B 23/00; A63B
23/0205; A63B 23/0216; A63B 23/0222
USPC .......................................... 602/19; 128/845
See application file for complete search history.

(56) References Cited

U.S. PATENT DOCUMENTS

| | | | |
|---|---|---|---|
| 603,004 A * | 4/1898 | Booth | A61F 5/24 |
| | | | 128/109.1 |
| 655,747 A | 8/1900 | Winckfield | |
| 2,529,258 A * | 11/1950 | Lobo | A61H 9/0078 |
| | | | 601/44 |
| 3,032,034 A * | 5/1962 | Jungmann | A61F 5/30 |
| | | | 128/104.1 |
| 3,078,842 A * | 2/1963 | Gray | A61H 9/0078 |
| | | | 601/44 |
| 4,444,191 A | 4/1984 | Harned | |
| 4,483,075 A | 11/1984 | Kundin | |
| 4,635,618 A | 1/1987 | Munz | |
| 5,007,895 A | 4/1991 | Burnett | |
| 5,295,481 A | 3/1994 | Geeham | |
| 5,807,280 A | 9/1998 | Davis | |
| 5,820,572 A | 10/1998 | Palmer | |
| D401,326 S | 11/1998 | Powell | |
| 5,865,722 A | 2/1999 | Heng | |
| 6,042,539 A | 3/2000 | Harper | |
| 6,098,205 A | 8/2000 | Schwartz et al. | |
| 6,146,362 A | 11/2000 | Turnbull et al. | |
| 6,159,167 A | 12/2000 | Hardin | |
| 6,254,614 B1 | 7/2001 | Jesseph | |
| 6,322,484 B1 * | 11/2001 | Muller | A63B 21/023 |
| | | | 482/140 |
| 6,394,977 B1 | 5/2002 | Taylor | |
| 6,409,638 B1 * | 6/2002 | Huston | A63B 23/0211 |
| | | | 482/112 |
| 6,475,124 B1 | 11/2002 | Weiss | |
| 6,485,467 B1 | 11/2002 | Crook | |
| 6,540,707 B1 | 4/2003 | Stark et al. | |
| 6,951,546 B2 | 10/2005 | Palmer et al. | |
| 7,229,422 B2 | 6/2007 | Klobe | |
| 7,401,413 B1 | 7/2008 | Nelson | |
| 2002/0022796 A1 | 2/2002 | Lawrence | |
| 2003/0220594 A1 | 11/2003 | Halvorson et al. | |
| 2004/0073150 A1 | 4/2004 | Roballey | |
| 2004/0243073 A1 | 12/2004 | Lockwood | |
| 2005/0119700 A1 | 6/2005 | Klobe | |
| 2006/0178601 A1 | 8/2006 | Wang et al. | |
| 2007/0066946 A1 | 3/2007 | Haggstrom et al. | |
| 2008/0058851 A1 | 3/2008 | Edelstein et al. | |
| 2009/0054929 A1 * | 2/2009 | Pajares Mellado | A63B 21/023 |
| | | | 606/246 |
| 2010/0137874 A1 | 6/2010 | Kim et al. | |
| 2010/0168630 A1 | 7/2010 | Cropper et al. | |
| 2011/0028898 A1 | 2/2011 | Clark, III et al. | |
| 2011/0172576 A1 | 7/2011 | Castro | |
| 2011/0230806 A1 * | 9/2011 | Lou | A61F 5/012 |
| | | | 602/13 |
| 2012/0116276 A1 | 5/2012 | Marinez Ferro et al. | |
| 2012/0209161 A1 | 8/2012 | Castro | |
| 2012/0302923 A1 | 11/2012 | Santiago | |
| 2013/0035611 A1 | 2/2013 | White | |
| 2013/0041303 A1 * | 2/2013 | Hopman | A61B 17/1322 |
| | | | 602/23 |
| 2013/0197315 A1 | 8/2013 | Foley | |
| 2013/0281272 A1 * | 10/2013 | Payne | A63B 23/0222 |
| | | | 482/140 |

* cited by examiner

VARIABLE PRESSURE UPPER TORSO BRACES AND METHODS RELATED THERETO

CROSS REFERENCE TO RELATED APPLICATIONS

This application claims priority benefit of U.S. Provisional Patent Application Ser. No. 61/734,310, filed on Dec. 6, 2012, the disclosure of which application is herein incorporated by reference in its entirety.

INTRODUCTION

Upper torso deformity such as pectus carinatum or costal margin flaring is treated with bracing to produce correction. The orthotic bracing relies on fixed constriction to limit upper torso expansion in the direction that is desired. The brace is mounted to a patient and rigidly set to a fixed diameter around the patient. The diameter of the brace remains fixed despite any changes in diameter of the upper torso (e.g., inhaling, exhaling, shrinkage of the deformity, loss of weight, etc.). If any of these changes are significant enough to require a change in diameter of the brace, the patient returns to the hospital or physician's office and the brace is resized at another, and more appropriate, fixed diameter.

SUMMARY

Upper torso braces to correct deformities in the upper torso of a patient are provided. The upper torso braces include a brace structure adapted to be maintained around an upper torso of an individual and to restrict outward expansion of the brace structure, and a variable force applicator coupled to the brace structure and positioned to contact and apply varying pressure to a target location on the upper torso. The brace structure is configured to restrict outward expansion to provide to enable the variable force applicator to apply variable pressure to the target location. In some instances, the upper torso braces may include a control element to manually adjust an amount of pressure provided by the variable force applicator to the target location. In some instances, the upper torso brace may include a brace structure adapted to be maintained around an upper torso of an individual and to restrict outward expansion of the brace structure, wherein the brace structure comprises a first non-flexible member and a second non-flexible member coupled together with retaining elements to maintain the first non-flexible member on a target location side of the upper torso and to maintain the second non-flexible member on a side of the upper torso opposite the target location side, wherein the target location side of the upper torso is an anterior side and the side of the upper torso opposite the target location side is a posterior side, and wherein the first non-flexible member and the second non-flexible member are adapted to be positioned on opposite extremes of the body of the individual and are each adapted to extend the width of the body of the individual; and a variable force applicator coupled to the brace structure and positioned to contact and apply varying pressure to a target location on the target location side of the upper torso, wherein the variable force applicator comprises: a contacting surface to contact the target location; a spring coupled to the contacting surface and to the first non-flexible member, wherein the spring is adapted to press the contacting surface towards the target location with pressure that varies with movement of the target location; and an adjustable control element to compress and decompress the spring to respectively increase or decrease an amount of pressure to the target location; wherein the brace structure is configured to restrict outward expansion of the brace structure to enable the variable force applicator to apply variable pressure to the target location.

Methods of correcting a deformity on an upper torso of a patient with the upper torso braces described herein are also provided. The methods include mounting the upper torso brace to an upper torso of a patient, positioning the variable force applicator to contact a target location of a deformity on the upper torso; and sizing the brace structure to secure the upper torso brace to the upper torso with an initial amount of pressure applied to the target location. The variable force applicator applies varying pressure to the target location on the upper torso.

DETAILED DESCRIPTION

Upper torso deformities (e.g., chest wall deformities such as pectus carinatum or costal margin flaring; or spinal deformities of the chest or abdomen area, such as occurs with scoliosis) may be treated with bracing to produce correction. The upper torso braces and methods disclosed herein relate to correction of upper torso deformities, such as chest deformities of the sternum or ribs as occurs with pectus carinatum or costal margin flaring, or spinal deformities of the spinal column as occurs with scoliosis, for example. The upper torso braces and methods related thereto apply a variable pressure to one or more deformities on a patient, such as a protrusion on the sternum or ribs for instance. While the upper torso braces and methods are described generally with respect to deformities such as occurs with pectus carinatum or costal margin flaring, the upper torso braces and methods described herein may also apply similarly to other upper torso deformity treatments, such as the treatment of scoliosis which may affect the chest and abdomen areas. With scoliosis, for instance, the target location may be the lateral chest wall instead of the frontal chest wall or the lateral abdomen area versus the front of the abdomen—e.g., to apply pressure on the convex side of the curvature to result in a straightening of the spine. While the deformity of the spinal column is internal to the body, it should be appreciated that references to the a part of the brace contacting the deformity (e.g., the contacting surface of the variable force applicator contacting the deformity) is meant to refer generally to the brace contacting the target location of the deformity on the body (e.g., the site on the body corresponding to the convex side of the curvature of the spine). Furthermore, it should be appreciated that references to the "upper torso" or "chest wall" are not meant to be limited to the front of the patient's body, but may also include the side and back of the patient's body—e.g., deformities on the side and back of the rib cage.

In some aspects of the present disclosure, upper torso braces are provided to correct deformities in the upper torso of a patient. The upper torso braces include a brace structure adapted to be maintained around a body of an individual and to restrict outward expansion, and a variable force applicator coupled to the brace structure and positioned to contact and apply varying pressure to a target location on the body. The brace structure is configured to restrict outward expansion to enable the variable force to apply variable pressure to the target location. In some instances, the upper torso braces may include a control element to manually adjust an amount of pressure provided by the variable force applicator to the target location.

As stated above, the brace structure is adapted to be maintained around a body of an individual and to restrict outward expansion. The upper torso brace includes one or more variable force applicators coupled to the brace structure and positioned to contact the body of the patient. The variable force applicators include stored energy which applies pressure outward toward the brace and inward toward the body of the patient, and because the brace structure is restricted in outward expansion, the resulting pressure from the variable force applicator is directed inward toward the target location on the body of the patient. For example, the variable force applicator may include an inflatable pressure chamber or spring loaded pad that is mounted to the brace structure to mold the upper torso (e.g., shrink or align a deformity) by applying pressure to the target location.

The variable force applicator may accommodate changes in upper torso size of the patient—e.g., due to breathing, shrinkage of the deformity, weight loss, etc. For example, the springs of the variable force application will elongate when upper torso size reduces (e.g., with correction of the deformity or expiration by the patient), but still provide correction pressure when the upper torso is reduced in size. Factors such as the spring wire diameter, number of coils chosen, etc. may be determined and chosen to provide adequate correction pressure with a reduction in upper torso size.

In some aspects, the target pressure may be selected by a physician or health care professional based on different factors, such as patient sensitivity (e.g., sensitivity to pain, skin sensitivity to irritation, etc.), location of the deformity (e.g., sternum, ribs, lateral chest, etc.), size and severity of the deformity, age of the patient, data from case studies, etc. With this in mind, for example, a pressure between 0.05 PSI to 30 PSI may be selected as the target pressure, such as a pressure between 0.1 to 18 PSI, and including a pressure between 0.2 and 6 PSI. For example, a target pressure may be selected as 1.5 PSI and the brace mounted to the patient such that the initial pressure provided is estimated to be near 1.5 PSI. The control member may thereafter be used to fine tune the initial pressure to achieve approximately 1.5 PSI of pressure applied to the deformity. The term "target pressure" is used broadly herein and may include a target range of pressures. For example, instead of the 1.5 PSI being the target pressure, the physician or health care provider may determine that the target pressure encompass the target pressure range of 1.25 PSI to 1.75 PSI.

Moreover, the variable pressure provided by the variable force applicator varies the pressure such that it fluctuates from the target pressure (e.g., 1.5 PSI in the example provided). For target pressures that encompass a target range, the fluctuations may remain within the target range, or in other instances, may extend outside the target range. The size of the fluctuations may depend on the type of variable force applicator used (e.g., whether based on springs, air, fluid, etc.), the inherent characteristics of the variable force applicator (e.g., the length of the spring, diameter of the spring, thickness of the spring, number of coils of the spring, the amount the spring is compressed, the amount the inflatable chamber is filled, the characteristics of the type of gas or fluid that is within the inflatable chamber, etc.), etc. Example sizes of fluctuations may vary depending on the application and target pressure, and may include, but are not limited to, fluctuations of 10 PSI or less, such as 5 PSI or less, including 1 PSI or less, or smaller.

In some instances, the physician or health care professional may select the appropriate size of the fluctuations for a specific patient, type or location of the deformity, or for any other specific circumstances of the case. For example, the physician or health care professional may choose from a number of commercial variable force applicators manufactured and sold with different predetermined or pre-calibrated characteristics as appropriate for the given patient, deformity, or set of circumstances. Moreover, the physician or healthcare professional may influence the size of the fluctuations via the control element—e.g., to control the amount of compression of the springs, or to control the amount of inflation of the inflatable chamber.

It should be appreciated that the above-provided pressures are exemplary, and that other target pressures may be implemented without compromising the underlying principles of the present disclosure. For example, case studies may be performed resulting in the determination of effective target pressures. Such target pressures are equally applicable to the underlying principles of the present disclosure.

The pressure applied by the variable force applicator automatically varies as with changes in upper torso size, such as from inhaling, exhaling, weight loss, shrinkage or alignment of the deformity, etc. Furthermore, as the upper torso (e.g., chest wall) deformity is significantly corrected over time, pressure on the deformity may be easily adjusted continuously by a control element of the variable force applicator. The adjustments may be made continuously at a remote location outside of the hospital or physician's office, such as at the home of the patient. In this way, the variable force applicator may be adjusted to maintain a target pressure without requiring a resizing of the brace structure, and without requiring the patient to return to the hospital or physician's office for adjustment of the brace structure. In certain embodiments, the variable force applicator is adjusted, as well as the brace structure resized (e.g., adjusting the flexible members or straps), by the patient or caretaker at the remote location to achieve the target pressure.

The brace structure may be made of non-flexible members, flexible members, or combination thereof. Further, in some embodiments, the brace structure may be made of inelastic materials, and in other embodiments, the brace structure may be made of elastic materials, or combinations of elastic and inelastic materials.

The term "non-flexible" and "flexible" are used herein to refer to the general rigidity of an object and the general ability of the object to bend without breaking. Further, the terms "elastic" and "stretchable" are used herein to refer to an object's general ability to be deformed by an external force (e.g., stretch) and then return to its original state after the external force is no longer applied. For example, a metal bar may be referred to as generally non-flexible and inelastic, and a rubber band may be referred to as generally flexible and elastic. The terms are used herein to refer to the general nature of an object and not meant as strict absolutes. Therefore, for example, a reference to being inelastic is meant to include being generally or approximately inelastic, such as having a negligible or in insignificant degree of elasticity.

In certain embodiments, the brace structure may include non-flexible members. The non-flexible members may be made from generally non-flexible materials including, but not limited to metals, metal-alloys, polymeric materials such as hard plastics, etc. In certain embodiments, the brace structure may include flexible members, such as, but not limited to straps made from flexible plastics, fabrics, etc. The straps, for example, may be used to join the non-flexible member to form the brace structure which is mounted and secured to the patient. The brace structure may be constructed to surround the body at the location of the target deformity and to restrict outward expansion of the brace structure. For example, the brace structure may be completely rigid and set to a fixed diameter. Alternatively, the brace structure may include a combination of non-flexible and flexible materials (e.g., straps) may enable the brace structure to be sized and secured to the patient quicker or more easily than a completely rigid brace structure. While the brace structure may include a combination of non-flexible and flexible materials, when secured to the patient, the brace structure restricts outward expansion of the brace structure—e.g., after being spread to its maximum circumference or diameter.

In certain embodiments, the brace structure may be made of inelastic materials to significantly restrict the outward expansion of the brace structure relative to the target deformity. In certain embodiment, the brace structure may include elastic materials but still adapted to provide adequate restriction to outward expansion of the brace. For example, the brace structure may include an elastic material that is stretched and wrapped around the patient's body at the target location to provide a tight or sufficiently snug fit, yet adequately resist further stretching and outward expansion of the brace structure. The brace structure may be constructed of a heavy canvas for example, or elastic polymeric materials, for example.

In some aspects, the variable force applicator provides variable pressure that varies with movement of the target location. The pressure from the variable force applicator is also variable in the sense that the pressure may be continuously adjusted by the patient or caretaker at a remote location (e.g., home) during the treatment process via the control element.

In certain embodiments, a variable force applicator includes one or more resilient biasing members that provide variable pressure to the target deformity on the body of the patient. Example resilient biasing members may include, but are not limited to, springs or other energy storing elements. For instance, a compression spring may be compressed to provide a force such as pressure to the target location. The force exerted by the spring is proportional to its change in length, and thus when the patient inhales or exhales, the circumference of the upper torso increases and decreases and changes the length or compression state of the spring. The variable force applicator may include, for example, one or more plates to transfer the energy from the spring to a contacting surface which is pressed against the target deformity.

In certain embodiments, the resilient biasing element may be adjusted via a control element while the brace structure is maintained at a fixed circumference or fixed maximum circumference at the target location. In this way, the amount of pressure may be increased or decreased to maintain a target amount of pressure to correct the deformity.

In certain embodiments, a variable force applicator includes one or more expandable members that provide variable pressure to the target deformity on the body of the patient. Expandable members may include, for example, an inflatable chamber or container that may be inflated with air or fluid. The inflatable pressure chamber may easily conform to irregular surfaces of the ribs, for example. While the spring loaded variable force applicator may also be used with irregular surfaces, the physician or health care practitioner may choose to use the spring loaded variable force applicator with smooth rib surfaces in a rigid chest wall, and the inflatable pressure chamber with irregular surfaces, for instance.

The variable force applicators may include positioning elements that enable the proper positioning and alignment of the variable force applicator on the bracing structure. Furthermore, the variable force applicator may include a control element to adjust the pressure provided to the target deformity—e.g., by adjusting the bias of the resilient biasing element, such as the compression of a spring; or by adjusting the expansion of an expandable member, such as an inflatable chamber. For example, a control element such as a fastener, dial, etc., that is used to compress or decompress the spring. For instance, a fastener may be screwed on the end of the alignment shaft extending out of two plates with the spring positioned between the plates and around the alignment shaft. The fastener may be adjusted to compress and decompress the spring. In certain embodiments, the control element may be in the form of a dial that the patient may turn to compress the spring. In some instances, the fastener and/or dial may include markings or other pressure indicators (e.g., predetermined or pre-calibrated) to inform the user of the pressure as to the approximate pressure while turning the dial and compressing the spring. In another embodiment, the control element may include a bulb pump which is used to inflate an inflatable chamber, and may also include a release valve for deflating the inflatable chamber.

While the control element may be used to adjust the pressure provided by the contacting surface of the variable force applicator to the target deformity, the control element may also be used to accommodate any changes in deformity size or upper torso size of the patient. For example, as the circumference of the patient becomes smaller, the resilient biasing element or inflatable chamber may be adjusted to displace the contacting surface closer to the patient, to result in a smaller net diameter for the brace, despite the brace structure remaining at the fixed circumference or fixed maximum circumference. In this way, the control element may be used to adjust the distance that the contacting surface of the variable force applicator extends from the bracing structure towards the body of the patient.

Furthermore, the control element may be used to adjust the distance that the contacting surface of the variable force applicator extends from the bracing structure towards the body of the patient, in order to accommodate any changes in upper torso size by the patient—e.g., from a shrinkage of the upper torso deformity, weight loss by the patient, mass changes from temperature changes, etc. Therefore, while the bracing structure may remain at the same diameter or circumference size initially set in the hospital or physician's office, the patient may adjust the distance the variable force applicator extends while at home to accommodate any changes in body size. This enables the target pressure to be maintained continuously and at the control of the patient or caretaker at a remote location such as the home of the patient. In other embodiments, the patient or caretaker adjusts the variable force applicator, as well as the brace structure (e.g., adjusting the flexible members or straps) to accommodate changes in upper torso size of the patient).

In certain embodiments, the variable force applicator includes a pressure gauge to indicate the amount of pressure provided against the target location on the patient's body. Any variety of pressure indication mechanism may be used, and may include electrical pressure sensors, mechanical pressure sensors, or combination thereof. The pressure gauges may be analog or digital pressure gauges. Digital pressure gauges may include, for example, pressure sensors positioned on the variable force applicator, for example, along with digital display.

In use, the brace is mounted onto the upper torso of the patient to correct one or more upper torso deformities. When mounted on the body of a patient, the variable force applicator is positioned to align with the target deformity on the patient's body. For example, with a deformity of the sternum, the variable force applicator is disposed against the sternum. The bracing structure is then sized and secured on the patient's body—e.g., at or near the target or desired pressure for correction of the deformity; or to remain snug against the body of the patient, providing a minimal initial amount of pressure. In some instances, the brace is sized and secured based on the patient's tolerance level to pressure—e.g., the level of discomfort felt by the patient at various pressures. The target or desired pressure to correct the deformity may thereafter be achieved by adjusting the control element.

As the brace structure restricts outward expansion of the brace, the variable pressure from the variable force applicator is directed towards the target deformity on the patient's body. The variable force applicator provides variable pressure that varies with movement of the target location. The pressure from the variable force applicator is also variable in the sense that the pressure may be continuously adjusted by the patient or caretaker at a remote location (e.g., home) during the treatment process via the control element. In certain embodiments, the pressure provided is localized to the general area of the target deformity or deformities, and thus only applies pressure to the area of the deformity or deformities.

It should be appreciated that the control elements may be mechanical, electrical, or combination thereof. For each type of control element, the patient may still manually adjust the pressure continuously via the mechanical, electrical, or electro-mechanical control element, whether it is tightening or loosening a fastener or dial, pumping a pump, pressing a switch or button, twisting a valve, etc.

In certain embodiments, the brace structure may be an elongated flexible material, such as canvas for example, used to encircle the body of a patient. The brace structure may include a securing element, such as Velcro, to secure the brace structure 410 when wrapped around the patient. Other securing elements such as, but not limited to, fasteners, buttons, buckles, clasp, clamps, ties, zippers, etc., may also be implemented in other embodiments.

The material of the brace structure may be elastic or non-elastic but should generally restrict outward expansion when wrapped and secured around the body of a patient. A non-elastic material may be used to completely restrict outward expansion, and an elastic material may be stretched when wrapped around the patient and secured in place to provide a tight or snug fit, while adequately resisting further stretching to provide sufficient restriction to outward expansion for the variable force applicator.

The brace structure may vary in length and width but should be long enough to encircle the body of a patient and wide enough to cover the target location of the deformity. In certain embodiments, the brace structure includes one or more variable force applicators positioned on the brace structure at location to contact the target deformities. The variable force applicators may be removably or permanently coupled to the bracing structure. For example, the variable force applicators may be either removably or permanently housed in pouches on the bracing structure, or may be fastened (e.g., Velcro, buttons, clips, ties, or other fastening device).

In one embodiment, the variable force applicators include expandable members such as inflatable chambers that are coupled to the bracing structure. In another embodiment, the variable force applicators may include springs and similarly attached to the bracing structure.

In certain embodiments, multiple expandable members may be implemented on the brace. For example, multiple expandable members may be positioned to contact multiple deformities on the body of a patient—e.g., one may be positioned to contact a protrusion of the sternum, while another may be positioned to contact a protrusion on the right side of patient's ribs.

The variable force applicators may also include a control element, including a pump and release valve for example, to adjust the inflation of the inflatable chamber. When multiple inflatable chambers are provided on the flexible bracing structure such as a canvas, for example, a single control element may be implemented to control all inflatable chambers together, or alternatively, multiple control elements may be implemented to control each inflatable chamber separately. Furthermore, one or more pressure gauge may also be implemented to monitor the pressure level of the one or more inflatable chambers together or independently.

In some aspects of the present disclosure, methods of correcting a deformity on a body of a patient are provided. The methods include mounting an upper torso brace disclosed herein to a body of a patient; positioning the variable force applicator to contact a target location of a deformity on the body; and sizing the brace structure to secure the upper torso brace to the body with an initial amount of pressure applied to the target location. The variable force applicator applies varying pressure to the target location on the body.

Further, the methods may include determining the target pressure to correct the deformity. This may include measuring or otherwise examining the protrusion. In certain embodiments, the variable force applicator includes a control element to manually adjust the amount of pressure provided by the variable force applicator to the target location. The health care practitioner or physician may, for example, use the control element to fine tune or adjust the initial amount pressure when the brace is first mounted to achieve the target pressure.

When mounting the bracing structure on the body of a patient, the variable force applicators are positioned and maintained on the deformities while the brace structure is sized and secured. When secured, the target or desired pressure to correct the deformity may thereafter be achieved by adjusting the state of the variable force applicator (e.g., the biasing of the resilient biasing member, or the expansion of the expandable member) via a control element—e.g., by compressing or decompressing springs, or by pumping a pump to inflate the inflatable chambers and activating a release valve to deflate the inflatable chambers.

The pressure provided by the brace may vary over time as the patient is wearing the brace. For example, the deformity may shrink as it is being corrected, the patient may gain or lose weight, etc. After the patient leaves the hospital or physician's office, the patient may monitor the pressure applied by the variable force applicator (e.g., via a pressure gauge) and adjust the pressure accordingly via the control element if the pressure is not within the target range. For example, the patient may pump air into an inflatable chamber to increase pressure and use a release valve to deflate air to reduce pressure. If the variable force applicator incorporates spring forces, the patient may adjust a control element to compress or decompress any springs to increase or decrease the pressure, respectively. In this way, the patient is not required to set up another appointment or go to the hospital or physician's office to have the pressure adjusted. This enables the patient to continuously monitor and adjust the pressure to maintain the target level of pressure needed for correction of the deformity.

Furthermore, the patient is able to adjust the position of the variable force applicator with respect to the diameter or circumference of the brace. In this way, any changes in the diameter or circumference of the upper torso of the patient may be accommodated by the patient adjusting the position of the variable force applicator via the control element. In this way, adjustments to the brace structure, which may in some instances be generally set to a fixed diameter or circumference, is not required.

Figure 1A:
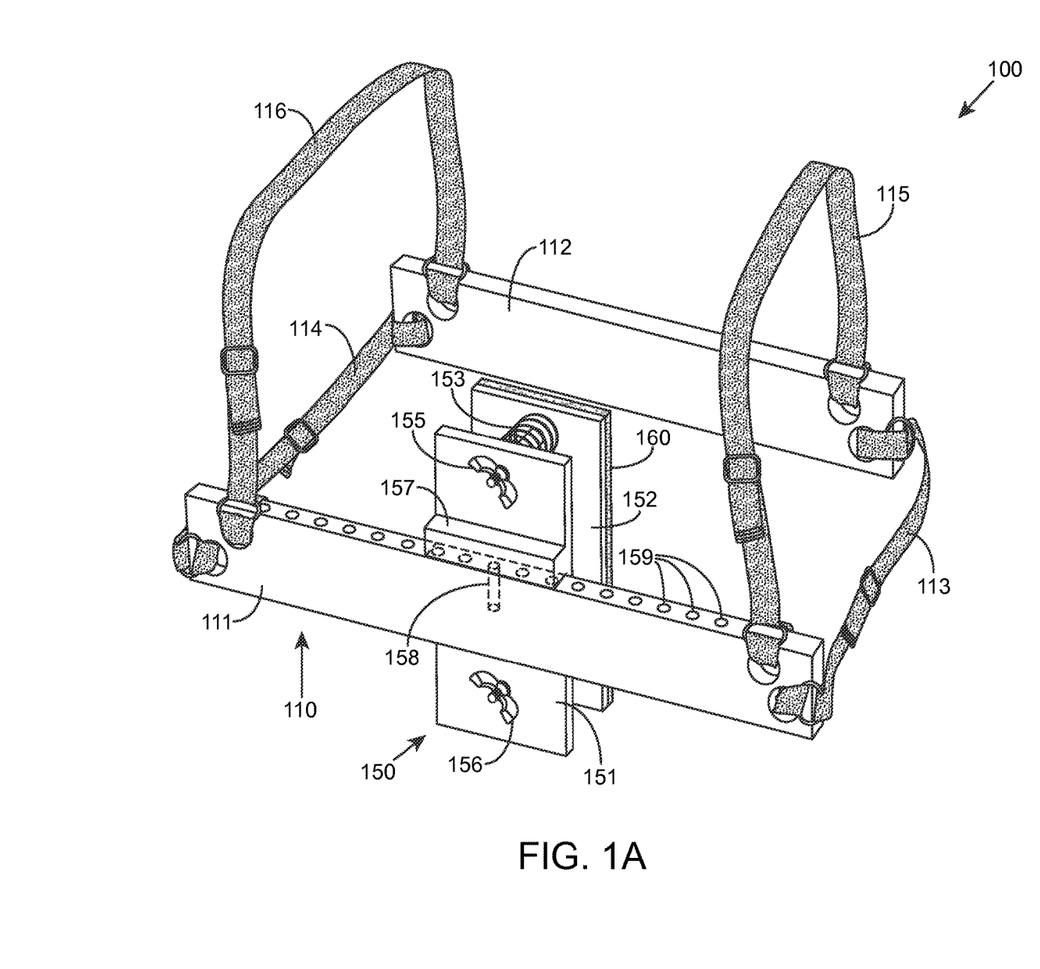
FIG. 1A illustrates a perspective view of an upper torso brace, according to one embodiment.
Figure 1B:
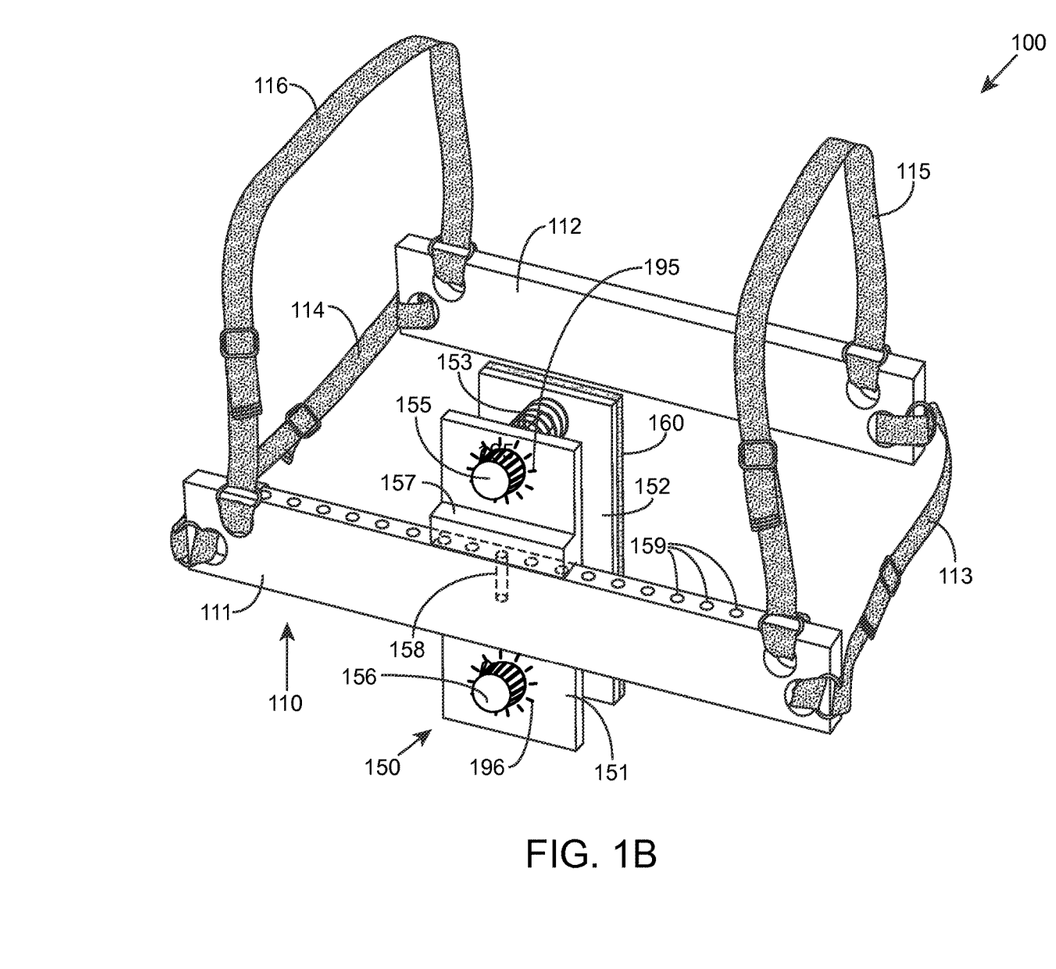
FIG. 1B illustrates a perspective view of an upper torso brace, according to one embodiment.
Figure 2A:
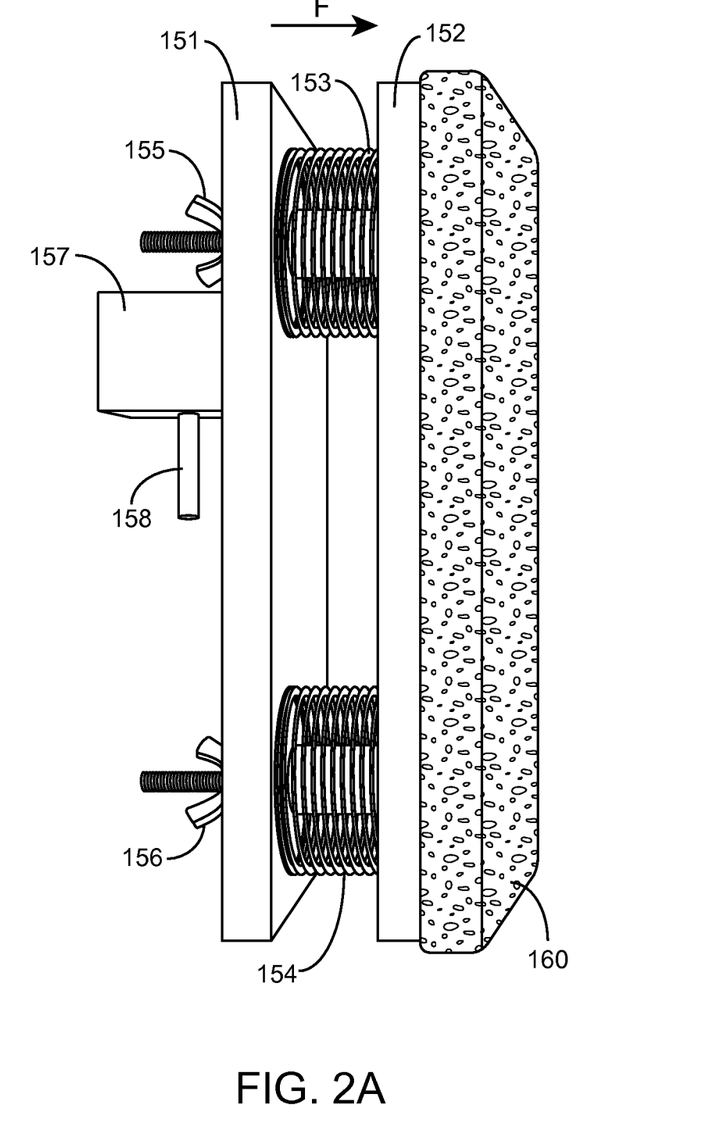
FIGS. 2A and 2B illustrates a side view of variable force applicator shown in FIG. 1 in an compressed and less compressed state, respectively, according to one embodiment.
Figure 2B:
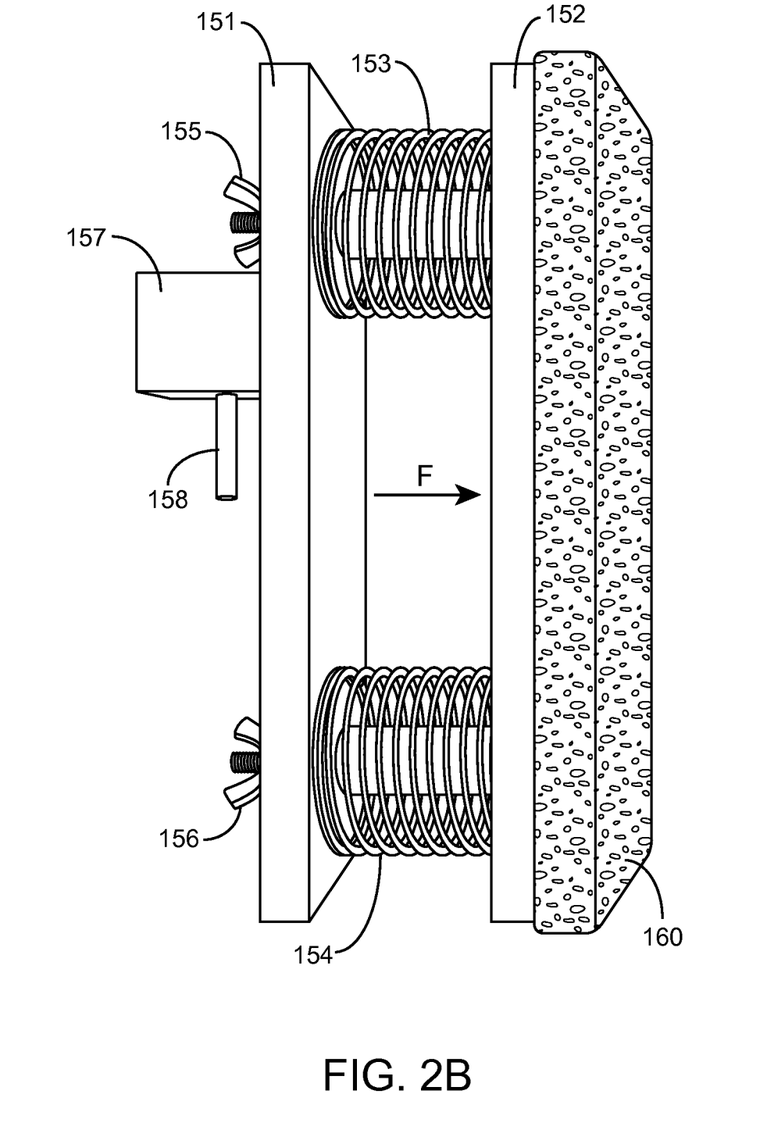

FIGS. 1A and 1B illustrate upper torso braces, according to certain embodiments of the present disclosure. The upper torso brace 100 is shown including a brace structure 110 and variable force applicator 150 coupled to brace structure 110. FIGS. 2A and 2B illustrate a side view of variable force applicator 150 shown in FIG. 1, and are described simultaneously below. FIG. 2A illustrates a side view of the variable force applicator when the springs are in a more compressed state than shown in FIG. 2B.

The brace structure 110 shown includes non-flexible members 111, 112, and retaining elements shown as side straps 113, 114 and shoulder straps 115, 116. Side strap 113 is coupled to and joins one end of each non-flexible member 111, 112, while side strap 114 is coupled to and joins the other end of each non-flexible member 111, 112. Shoulder strap 115 is also coupled to and joins one end of each non-flexible member 111,112, while should strap 116 is coupled to and joins the other end of each non-flexible member 111, 112. For example, when mounted on the body of a patient, the non-flexible members 111, 112 and side straps 113, 114 surround the body of the patient with the non-flexible member 111 along the patient's frontal chest and the non-flexible member 112 along the patient's back, and side straps 113, 114 along the left and right sides, respectively, of the patient's chest below their arms. Shoulder straps 115, 116 extend over the left and right shoulder to retain the brace 100 in the vertical direction. Each of the straps 113, 114, 115, 116 may include adjustable fastening elements 117 to adjust the length of the straps to secure brace 101 on the patient's body. Any variety of adjustable fastening elements may be used in other embodiments. It should be appreciated that in other embodiments, the non-flexible members may be positioned elsewhere (e.g., on the lateral chest) to accommodate target deformities at other locations.

The variable force applicator 150 is coupled to the inside of non-flexible member 111 of brace structure 101 and positioned to contact a deformity at a target location on the body of a patient (not shown). The variable force applicator is shown positioned approximately in the center of non-flexible member 111 in order to contact a deformity in the approximate center of the upper torso wall, such as a protrusion of the sternum as occurs with pectus carinatum, for example.

Variable force applicator 150 includes plates 151, 152 and resilient biasing elements 153, 154 shown as springs. Plate 151 is coupled to the non-flexible member 111 and is shown including positioning element 157 that is used to couple plate 151 to an appropriate location on non-flexible member 111. Positioning element 157 includes a protruding member 158 which inserts into one of the alignment holes 158 along the top edge 160 of non-flexible member 111. In this way, a health care professional may adjust the horizontal position of the force applicator 150 to properly align with the target location on the body. It should be appreciated that the alignment mechanism shown is exemplary and that other alignment mechanisms may be implemented in other embodiments.

Plate 152 is shown including a contacting surface 160 which contacts and applies pressure to the target deformity. The contacting surface 160 may be a surface on plate 152 or, as shown in the embodiment, be an additional layer added to plate 152 for purposes such as comfort (e.g., padding), sanitation, etc. The contacting surface may be made from any variety of hard materials, such as metals, metal alloys, polymeric materials such as hard plastics; and/or soft materials, such as fabrics, foam, polymeric materials such as soft plastics, rubber, etc.

Springs 153, 154 are disposed between plates 151, 152 and coupled to each plate 151, 152. While the embodiment shown include two springs, in other embodiments, a different number of springs may be implemented, such as one spring, three springs, four springs, etc. The springs 153, 154 may be removably or fixedly attached to plates 151, 152 by any variety of mechanisms. In the embodiment shown, an alignment shaft (not shown), such as a bolt, screw, etc., is disposed through plate 152, through the center of spring 153, and through plate 151. Brace 100 also includes control elements 155, 156 that enable a user to compress and decompress the spring to adjust the amount of pressure provided. In FIG. 1A, a control element 155 is a fastener that is screwed on the end of the alignment shaft extending out of plate 151 to secure the alignment shaft to the plates 151, 152. Furthermore, control element 155 may be manually tightened to compress spring 153 or loosened to decompress spring 153. For example, the health care professional and/or the patient may use the control element 155 to manually adjust the compression of the spring 153 to increase or decrease the amount of pressure provided by the spring. A second alignment shaft (not shown) and control element 156 is similarly structured for spring 154, and for the sake of brevity is not repeated again. FIG. 1B illustrates another embodiment of the brace 100 shown in FIG. 1A, except the control elements 155 and 156 are in the form of dials. Other embodiments may include other forms of control elements used to compress or decompress the springs.

In one embodiment, control elements 155, 156 may be configured to indicate the pressure by the spring—e.g., with markings (e.g., shown in FIG. 1B as markings 195, 196) that indicate pressure levels that have been pre-calibrated or pre-measured during manufacturing for instance. For example, pre-calibrated or pre-measured markings may be indicated on the variable force applicator next to the control elements 155, 156 (e.g., in the form of a fastener or dial which is turned to compress or decompress the springs) to indicate the level of pressure provided as the control element is adjusted. In another embodiment, the variable force applicator may include a pressure gauge to indicate the amount of pressure provided against the target location on the patient's body. Any variety of pressure indication mechanism may be used, such as mechanical pressure sensor or electro-mechanical pressure sensors. For example, a pressure sensor may be disposed at a location on the variable force indicator (e.g., on one of the plates 151, 152) and coupled to an electronic circuit including a pressure readout for the patient.

In use, the brace 100 is mounted onto the upper torso of the patient with the contacting surface of the variable force applicator against the target deformity to correct one or more upper torso deformities. When mounted on the body of a patient, the non-flexible members 111, 112 and side straps 113, 114 surround the body of the patient. Non-flexible member 111 along the patient's body with the variable force applicator 150 disposed between the non-flexible member 111 and the patient's body. The variable force applicator 150 is positioned to align the contacting surface with the target deformity on the patient's body. For example, with a deformity of the sternum, the non-flexible member 111 is positioned in the front of the patient's chest with the contacting surface 160 of the variable force applicator 150 disposed against the sternum. Non-flexible member 112 is disposed along the patient's back, and side straps 113, 114 around the left and right sides, respectively, of the patient's chest below their arms. Shoulder straps 115, 116 are extended over the left and right shoulders to retain the brace 100 in the vertical direction. The adjustable fastening elements 117 are then adjusted to provide the proper length of the straps to size and secure brace 101 on the patient's body. The straps 113, 114, 115, 116 may be adjusted to provide an initial amount of pressure—e.g., at or near the target or desired pressure for correction of the deformity; or to remain snug against the body of the patient, providing a minimal initial amount of pressure. In some instances, the brace is sized and secured based on the patient's tolerance level to pressure—e.g., the level of discomfort felt by the patient at various pressures. The target or desired pressure to correct the deformity may thereafter be achieved by adjusting the potential energy in the resilient biasing elements 153, 154 via control elements 155, 156—e.g., by tightening fasteners 155, 156 to adjust the compression level of springs 153, 154. In some instances, resilient biasing elements 153, 154 may be biased to an initial pressure setting via the control element 155 before the brace 101 is mounted to the patient's body.

The non-flexible members 111, 112 and side straps 113, 114 surround the body of the patient to restrict the outward expansion of the brace. Therefore, the potential energy from springs 153, 154 causes pressure to be directed toward each plate 151, 152. As plate 151 is coupled to brace structure 101, which is restricted in outward expansion, the resulting force F from the springs 153, 154 presses plate 152 towards the target deformity on the patient's body. Springs 153, 154 provide a varying pressure that varies with movement of the target location. For example, when the patient inhales or exhales, the circumference of the upper torso increases and decreases, respectively. The force F in FIG. 2A will be greater than the force F in FIG. 2B because the springs 153, 154 are in a more compressed stated in FIG. 2A. Moreover, the springs 153, 154 provide some give to accommodate the change, yet still maintain pressure against the deformity. This also applies should the patient increase or decrease in size due to weight gain or loss or from temperature changes, etc. For example, as the deformity gets smaller, the springs 153, 154 automatically expand and continue to provide pressure to the target location.

The pressure from the springs 153, 154 is also variable in the sense that the pressure may be continuously adjusted by the patient during the treatment process via the control elements 155, 156. For example, in some instances, the pressure applied by the brace may drop below the target (e.g., when the deformity decreases in size over time, or should the patient lose weight). In such case, for instance, the patient may adjust the control elements 155, 156 to increase the pressure applied to the deformity to provide the target amount of pressure for correction of the deformity. In some instances, for example, as the deformity shrinks, the circumference of the patient's upper torso may be reduced, and the patient or caretaker may increase the distance of the variable force applicator to accommodate the reduced upper torso circumference—e.g., elongate or decompress the springs to accommodate the reduction in torso circumference.

Figure 3A:
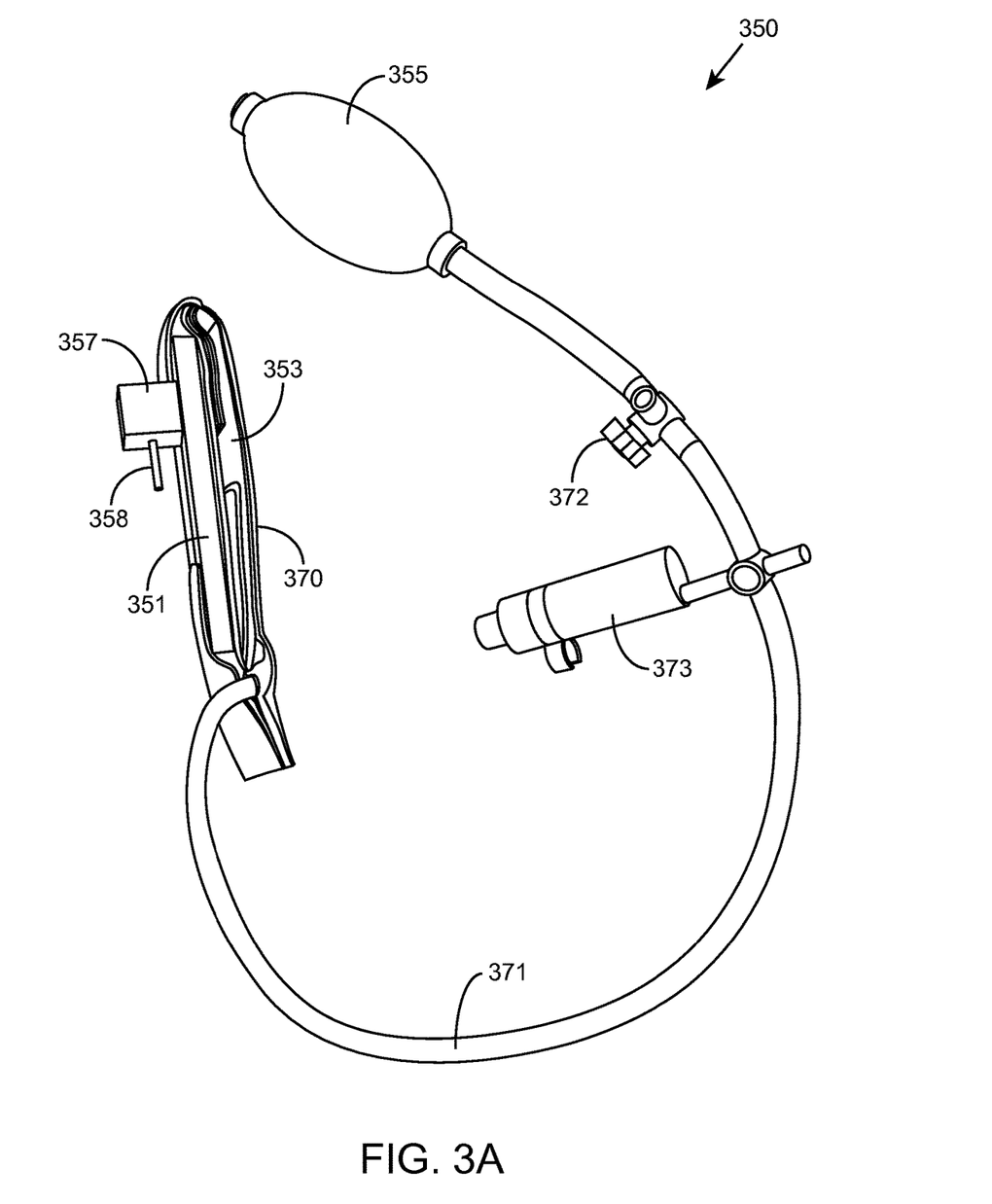
FIGS. 3A and 3B illustrates a side view of a variable force applicator in a deflated and inflated state, respectively, according to one embodiment.
Figure 3B:
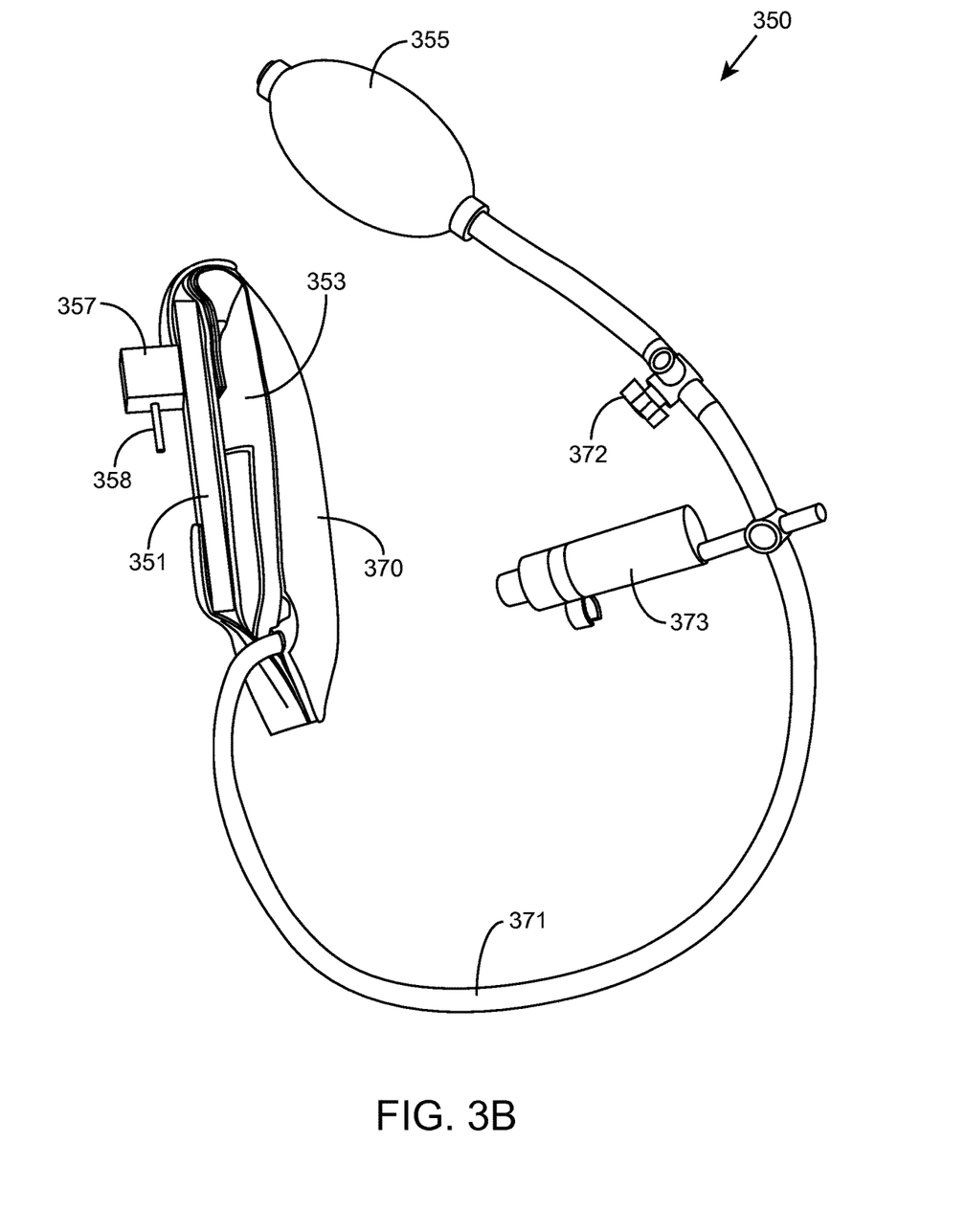

FIGS. 3A and 3B illustrate a side view of a variable force applicator 350, according to another embodiment. The variable force applicator 350 is coupled to the inside of non-flexible member 111 of brace structure 101 and positioned to contact a deformity at a target location on the body of a patient, similar to variable force applicator 150 shown in FIG. 1 and described above. Variable force applicator 350 includes plate 351 that is coupled to the non-flexible member 111 and is shown including positioning element 357 that is used to couple plate 351 to an appropriate location on non-flexible member 111, as similarly described for plate 151 and positioning element 157 in FIG. 1. Positioning element 357 includes a protruding member 358 which inserts into one of the alignment holes 158 along the top edge 160 of non-flexible member 111 to enable proper alignment with the target location on the body.

Variable force applicator 350 includes an expandable member 353 that is coupled to plate 351. The expandable member 353 may be removably coupled to plate 351 (e.g., via Velcro, snaps, hooked, etc.) or permanently coupled to plate 351 (e.g., glued, adhered, etc.). In the embodiment shown, the expandable member 353 is coupled to the brace structure 101 via plate 351 and positioned to apply pressure to the target deformity. A contacting surface 370 of expandable member 353 contacts the target location. The expandable member 353 shown is an inflatable chamber or container that can be filled with air. In other embodiments, fluid may be used to fill the chamber or container. The inflatable chamber may be made with any variety of materials (e.g., latex, rubber, other polymeric material, etc.) but should be able to contain and maintain air (or fluid in other embodiments) without significant or rapid loss. Because the inflatable chamber 353 is filled with air (or fluid in other embodiments) and thus gives when compressed, the inflatable chamber 353 provides varying pressure as the patient's upper torso expands. Thus, as the patient's upper torso expands and contracts, the pressure from the inflatable chamber 353 varies but is maintained against the target deformity. FIG. 3A, illustrates the inflatable chamber 353 in a generally deflated state, while FIG. 3B illustrates the inflatable chamber 353 in a completely inflated stated.

Variable force applicator 350 also includes control element 355 coupled to the expandable member 353 via tubing 371. Control element 355 is shown as a hand pump or bulb pump that pumps air through tubing 371 into inflatable chamber 353 for expansion. Variable force applicator 350 also includes a release valve 372 disposed in tubing 371 between the pump 355 and inflatable chamber 353, which serves as a control element to release air from the inflatable chamber to shrink the inflatable chamber 353.

A pressure gauge 373 is also shown disposed in tubing 371 to indicate the amount of pressure provided to the inflatable chamber 353. The pressure gauges in other embodiments may be analog or digital pressure gauges. Digital pressure gauges may include, for example, pressure sensors and digital displays. The health care professional or user may monitor the pressure gauge and adjust the amount of pressure provided to the target deformity via the pump 355 and release valve 372. Furthermore, the patient may monitor the pressure and continuously maintain a target or desired pressure for correction of the deformity without having to return to the hospital or physician's office. In some instances, the target or desired pressure may change, for example at one or more times throughout the correction process.

In use, the brace 100 is mounted onto the upper torso of the patient with the contacting surface of the variable force applicator against the target deformity to correct one or more upper torso deformities, as similarly described for the brace including variable force applicator 150. The brace structure is sized and secured, and the target or desired pressure to correct the deformity may thereafter be achieved by adjusting the amount of expansion of the expandable member 353 via control element 355—e.g., by pumping pump 355 to inflate the inflatable chamber 353. In some instances, inflatable chamber 353 may be partially inflated via the pump 355 before the brace 101 is mounted to the patient's body.

Again, the non-flexible members 111, 112 and side straps 113, 114 surround the body of the patient to restrict the outward expansion of the brace. Therefore, as the inflatable chamber 353 fills with air, the chamber 353 expands. As inflatable chamber 353 is coupled to brace structure 101, which is restricted in outward expansion, the resulting force from the expansion of the inflatable chamber 353 is directed towards the target deformity on the patient's body. Inflatable chamber 353 includes a contacting surface 370 that contacts the target location to provide a varying pressure that varies with movement of the target location. For example, when the patient inhales or exhales, the circumference of the upper torso increases and decreases, respectively. The air in the inflatable chamber 353 provides some give to accommodate the change, yet still maintains pressure against the deformity. This also applies should the patient increase or decrease in size due to weight gain or loss or from temperature changes, etc. For example, as the deformity gets smaller, the inflatable chamber automatically expands slightly and continues to provide pressure to the target location The pressure from the inflatable chamber 353 is also variable in the sense that the pressure may be continuously adjusted by the patient or caretaker during the treatment process at a remote location (e.g., the home of the patient) via the control elements 355 and 372. For example, in some instances, the pressure applied by the brace may drop below the target (e.g., when the deformity decreases in size over time, or should the patient lose weight). In such case, for instance, the patient may adjust the control element 355 to increase the pressure applied to the deformity to provide the target amount of pressure for correction of the deformity. In some instances, for example, as the deformity shrinks, the circumference of the patient's upper torso may be reduced, and the patient or caretaker may increase the distance of the variable force applicator to accommodate the reduced upper torso circumference—e.g., elongate or decompress the springs to accommodate the reduction in torso circumference, or inflate the inflatable chamber to accommodate the reduction in torso circumference. For example, when the deformity decreases in size over time, or should the patient lose weight, the patient may adjust control element 355 to increase the pressure applied to the deformity, or adjust control element 372 to decrease the pressure applied to the deformity, in order to maintain the target amount of pressure for correction of the deformity. The control element 355 may also be used to adjust the distance of the variable force applicator from the bracing structure to accommodate any changes in patient upper torso size to the target location.

It should be appreciated that in other embodiments, the control elements disclosed herein may be mechanical, electrical, or combination thereof. For the particular method implemented, the patient or caretaker may still manually adjust the pressure continuously via the mechanical, electrical, or electro-mechanical control element, whether it is tightening or loosening a fastener, pumping a pump, pressing a switch or button, twisting a valve, etc.

Figure 4:
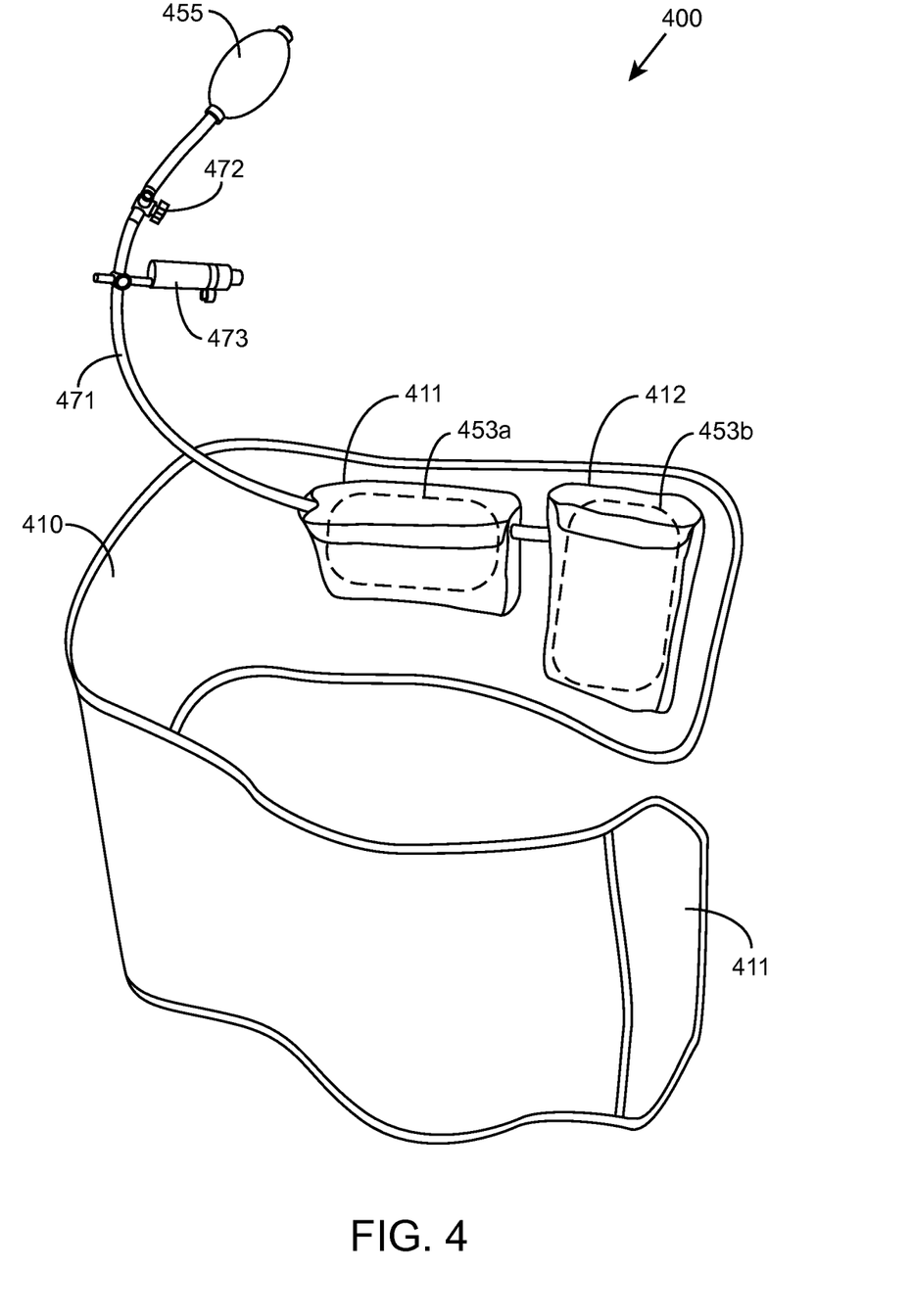
FIG. 4 illustrates an upper torso brace, according to one embodiment.

FIG. 4 illustrates an upper torso brace, according to another embodiment. The upper torso brace 400 is shown including a brace structure 410 and variable force applicator 450 coupled to brace structure 410. The brace structure 410 includes a flexible material, such as, but not limited to, canvas or other fabric material.

The brace structure 410 shown is an elongated flexible material used to encircle the body of a patient. The brace structure 410 includes a securing element 411 which is used to secure the brace structure 410 when wrapped around the patient. In the embodiment shown, Velcro is used as the securing element 411 and is positioned on the inside of the brace structure to face the body of the patient and to attach to the outside of the brace structure 410 when wrapped. For example, securing element 411 may comprise Velcro hooks which fasten to Velcro loops disposed on the corresponding location on the outside of the brace structure 410. In some instances, the material of the brace structure 410 may be chose to adequately function as Velcro loops and adhere to the Velcro hooks 411. Other securing elements such as, but not limited to, fasteners, buttons, buckles, clasp, clamps, ties, zippers, etc., may also be implemented in other embodiments without compromising the underlying principles of the present disclosure.

The material may be elastic or non-elastic but should generally restrict outward expansion when wrapped and secured around the body of a patient. A non-elastic material may be used to completely restrict outward expansion. An elastic material may be stretched when wrapped around the patient and secured in place to provide a tight or snug fit, while adequately resisting further stretching to provide sufficient restriction to outward expansion.

The brace structure 410 may vary in length and width but should be long enough to encircle the body of a patient and wide enough to cover the target location of the deformity. Brace structure 410 is shown including two pouches 411, 412 and retaining element 413 each located on the inside of the brace structure which faces the body of the patient as the brace structure 410 is wrapped around the body of the patient.

Brace 400 also includes a variable force applicator 450 including expandable members 453a, 453b, which are housed in the two pouches 411, 412, respectively. The two pouches 411, 412 and respective expandable members 453a, 453b are positioned to contact two deformities on the body of a patient. For example, expandable members 453a may be positioned to contact a protrusion of the sternum, while expandable members 453b may be positioned to contact a protrusion on the right side of patient's ribs. The position of the two pouches 411, 412 and respective expandable members 453a, 453b are exemplary, and may vary in position in other embodiments. In some instances, the expandable members 453a, 453b are removably disposed in the pouches 411, 412 such that the expandable members 453a, 453b may easily be removed for replacement or to permit the brace structure 410 to be cleaned, for example.

In another embodiment, the expandable members 453a, 453b are directly coupled to the brace structure 410 without a pouch. For example, the expandable members 453a, 453b may be fastened (e.g., via Velcro, buttons, clamps, sewn, etc.) to the brace structure. In some instances, the expandable members 453a, 453b are removably coupled to the brace structure to vary their locations to coincide with the target deformities.

While two pouches and respective expandable members 453a, 453b are included in the embodiment shown, it should be appreciated that other numbers of pouches and respective expandable members may be used in other embodiments— e.g., one, three, four, five, etc. Furthermore, while the embodiment shown includes pouches 411, 412 which house the expandable members 453a, 453b, in other embodiments the expandable members 453a, 453b may be coupled to the brace structure 410, such as with Velcro, buttons, clips, ties, or other fastening device.

In the embodiment shown, the expandable members 453a, 453b are inflatable chambers which are fillable with air. In another embodiment, the inflatable chamber may be filled with fluid. The variable force applicators 450 also include a control element (e.g., pump 455 and release valve 472) coupled to the inflatable chambers 453a, 453b via tubing 471. Control element 455 is shown as a bulb pump which can be pumped by hand to pump air into the inflatable chambers 453a, 453b to inflate and expand the chambers 453a, 453b. The variable force applicators 450 also includes a control element 471 in the form of a release valve 471 to release air from the chambers 453a, 453b to deflate and shrink the chambers 453a, 453b. While in the embodiment shown, a single pump 455 and release valve 471 are used for both inflatable chambers 453a, 453b, in other embodiments each inflatable chamber may be coupled to separate pairs of pump and release valve for independent control of each inflatable chamber.

As shown in FIG. 4, the variable force applicator 450 may also include a pressure gauge 473 disposed in tubing 471 to indicate the amount of pressure provided to the inflatable chambers 453a, 453b, as similarly shown and described for FIG. 3. The health care professional or user may monitor the pressure gauge and adjust the amount of pressure provided to the target deformity via the pump 455 and release valve 472. Furthermore, the patient may monitor the pressure and continuously maintain a target or desired pressure for correction of the deformity without having to return to the hospital or physician's office. In another embodiment, each inflatable chamber may include a separate pressure gauge for independent monitoring.

When mounting the brace 400 on the body of a patient, the variable force applicators 450a, 450b are positioned and maintained on the deformities while the remainder of the brace structure is wrapped around the body of the patient. When completely wrapped around the patient, the brace structure 410 is secured in place by securing element 411. The target or desired pressure to correct the deformity may thereafter be achieved by adjusting the amount of expansion of the expandable members 453a, 453b via control element 455—e.g., by pumping pump 455 to inflate the inflatable chambers 453a, 453b. In some instances, inflatable chambers 453a, 453b may be partially inflated via the pump 455 before the brace 400 is mounted to the patient's body.

The brace structure 410 surrounds the body of the patient to restrict the outward expansion of the brace. Therefore, as the inflatable chambers 453a, 453b fill with air, the inflatable chambers 453a, 453b inflate and expand. As inflatable chambers 453a, 453b are coupled to brace structure 410, which is restricted in outward expansion, the resulting force from the expansion of the inflatable chambers 453a, 453b is primarily directed inward towards the target deformity on the patient's body. Inflatable chambers 453a, 453b include contacting surfaces that contact the target location to provide a varying pressure that varies with movement of the target location. Furthermore, the pressure from the inflatable chambers 453a, 453b are also variable in the sense that the pressure may be continuously adjusted by the patient during the treatment process via the control elements 455 and 472—e.g., pump 455 and release valve 472, as similarly described for the inflatable chamber in FIG. 3.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. An upper torso brace comprising:
   a brace structure adapted to be maintained around an upper torso of an individual and to restrict outward expansion of the brace structure, wherein the brace structure comprises a first non-flexible member and a second non-flexible member coupled together with retaining elements adapted to maintain the first non-flexible member on a target location side of the upper torso and adapted to maintain the second non-flexible member on a side of the upper torso opposite the target location side, wherein the target location side of the upper torso is an anterior side and the side of the upper torso opposite the target location side is a posterior side, and wherein the first non-flexible member and the second non-flexible member are adapted to be positioned on opposite extremes of the body of the individual and are each adapted to extend the width of the body of the individual; and
   a variable force applicator coupled to the brace structure and positioned to contact and apply varying pressure to a target location on the target location side of the upper torso, wherein the variable force applicator comprises:
   a contacting surface to contact the target location;
   a spring coupled to the contacting surface and to the first non-flexible member, wherein the spring is adapted to press the contacting surface towards the target location with pressure that varies with movement of the target location; and
   an adjustable control element adapted to compress and decompress the spring to respectively increase or decrease an amount of pressure applied to the target location;
   wherein the brace structure is configured to restrict outward expansion of the brace structure to enable the variable force applicator to apply variable pressure to the target location.

2. The upper torso brace of claim 1, wherein the variable force applicator comprises a pressure gauge for indicating a relative pressure applied to the target location.

3. The upper torso brace of claim 1, wherein the retaining elements are flexible straps coupled to corresponding ends of the first and second non-flexible members, and wherein the flexible straps resist stretching from the first non-flexible member to the second non-flexible member.

4. A method of correcting a deformity on an upper torso of a patient, the method comprising:
   mounting the upper torso brace according to any one of claims 1, 2, and 3 to an upper torso of a patient;
   positioning the variable force applicator to contact the target location on the target location side of the upper torso;
   sizing the brace structure to secure the upper torso brace to the upper torso with an initial amount of pressure applied to the target location on the target location side of the upper torso;
   wherein the variable force applicator applies varying pressure to the target location on the target location side of upper torso.

5. The method of claim 4, further comprising:
   determining a target pressure to be applied to the target location on the target location side of the upper torso for correction of the deformity; and
   adjusting the adjustable control element to adjust the initial amount of pressure to achieve the target pressure.

6. The method of claim 5, further comprising:
   monitoring the amount of pressure applied to the target location on the target location side of the upper torso; and
   adjusting the adjustable control element to achieve a target pressure without adjusting a circumference size of the brace structure.

* * * * *